United States Patent [19]
Huber

[11] Patent Number: 5,810,591
[45] Date of Patent: Sep. 22, 1998

[54] LINK BETWEEN A DENTAL IMPLANT AND AN ARTIFICIAL TOOTH AND METHOD FOR PRODUCING

[76] Inventor: Peter Huber, Haselweid 20, Münchwilen CH-9542, Switzerland

[21] Appl. No.: 849,562
[22] PCT Filed: Nov. 16, 1995
[86] PCT No.: PCT/CH95/00269
  § 371 Date: May 14, 1997
  § 102(e) Date: May 14, 1997
[87] PCT Pub. No.: WO96/17559
  PCT Pub. Date: Jun. 13, 1996

[30]     Foreign Application Priority Data

Apr. 12, 1997  [CH]  Switzerland .................. 3637/94

[51] Int. Cl.[6] ........................................ A61C 8/00
[52] U.S. Cl. .............................. 433/172; 433/173
[58] Field of Search ................... 433/172, 173, 433/174

[56]     References Cited

U.S. PATENT DOCUMENTS

| | | | |
|---|---|---|---|
| 4,907,969 | 3/1990 | Ward | 433/173 |
| 4,976,739 | 12/1990 | Duthie, Jr. | 433/174 |
| 5,092,770 | 3/1992 | Zakula | 433/172 |
| 5,417,570 | 5/1995 | Zuest et al. | 433/172 |
| 5,417,692 | 5/1995 | Goble et al. | 433/173 |
| 5,443,467 | 8/1995 | Biedermann et al. | 606/65 |

FOREIGN PATENT DOCUMENTS 9309728  5/1993  WIPO .

*Primary Examiner*—John J. Wilson
*Attorney, Agent, or Firm*—Martin A. Farber

[57]     ABSTRACT

A link to be inserted between a dental implant in a jaw and an artificial tooth, comprising a first screw bolt for fastening the link on the dental implant, and a head portion in the form of a second screw bolt for fastening a tooth holding sleeve. The screw bolts are formed as a unitary one-piece construction, where the mutual angular orientation of both screw bolts is adapted to the jaw, on the one hand, and to the orientation of the artificial tooth, on the other hand.

20 Claims, 1 Drawing Sheet

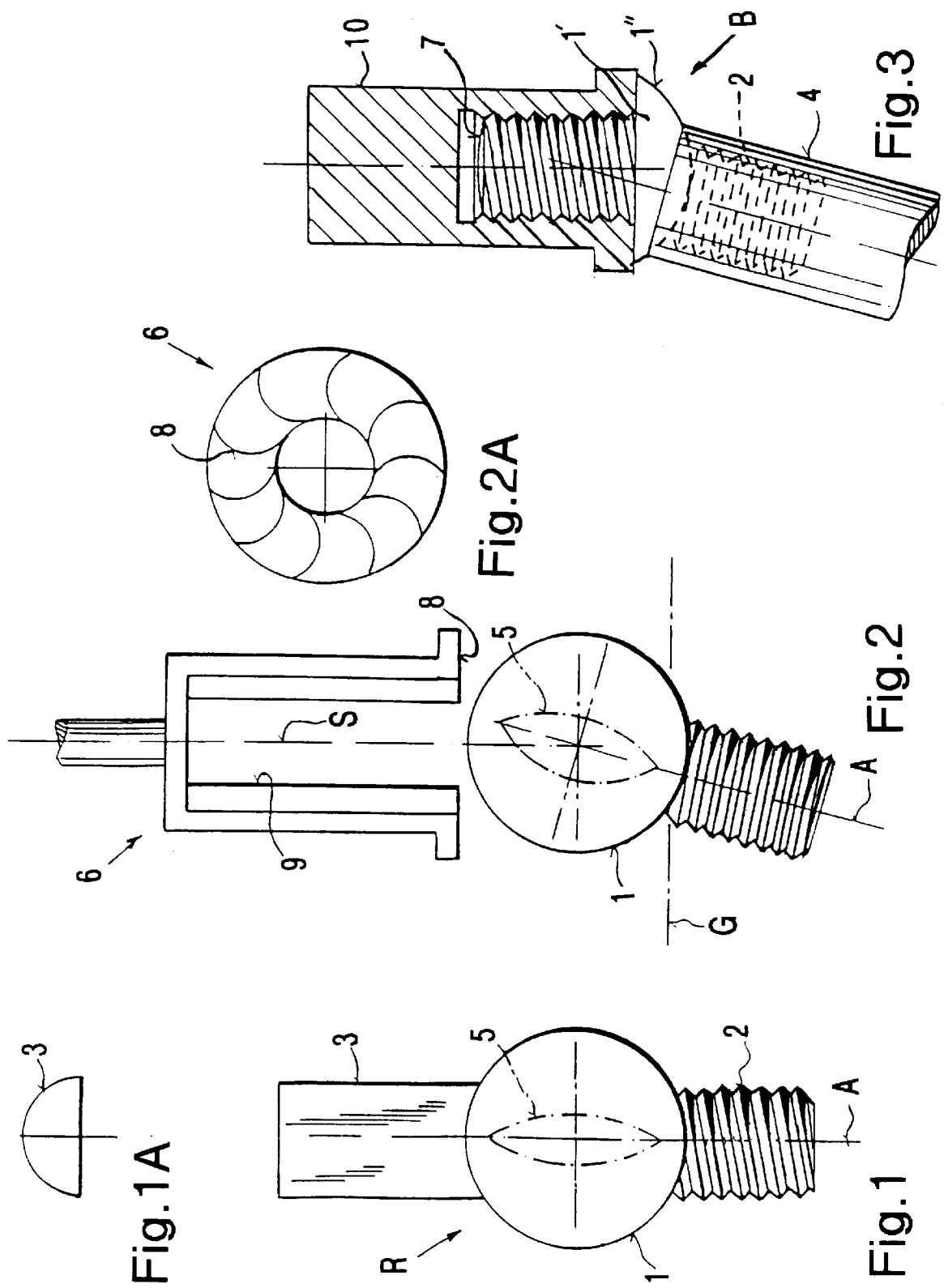

5,810,591

LINK BETWEEN A DENTAL IMPLANT AND AN ARTIFICIAL TOOTH AND METHOD FOR PRODUCING

FIELD AND BACKGROUND OF THE INVENTION

The invention relates to a link between a dental implant in a jaw and an artificial tooth as well as a method for producing same.

When joining artificial teeth, such as a tooth bridge, to a jaw implant, a problem results if the jaw has grown angled to a horizontal plane inconsistent with the angle of the teeth. Therefore, a link is necessary by which the difference of angles is compensated. In the past, it has been found that adaptation of such links is difficult due to orientations of teeth at very different angles in different patients. Certainly, one has tried to form a head portion as an adjustment ball to which a tooth sleeve forming a hollow sphere is clamped. It should be noted, however, that the forces occurring on a jaw are very high for which reason the clamped tooth sleeve may easily become loose again. Examples of such adjustment facilities can be derived from U.S. Pat. Nos. 5,092,770 and 5,417,570 and 5,443,467 issued within the priority period.

SUMMARY OF THE INVENTION

Therefore, it is an object of the invention to construct a link of the kind mentioned in the outset in a tough and simple manner, taking into account, nevertheless, the individual angular position of a jaw implant and the angle of the tooth.

In accordance with the invention, due to the fact that both screw bolts, thus, will form an integral part of a unit, subsequent adjustment and clamping becomes unnecessary so that a tough and strong construction is warranted. The individual angular position of jaw implant and angle of the tooth is considered, thereby, by forming the two screw bolts under the respective angle.

Theoretically, this would be possible by measuring the angle and reproducing them in the two bolts, such as by a casting process or another shaping process. Advantageous is, however, the manufacture of the link according to the invention.

The present invention also avoids problems with placing a machining tool under an angle to a first screw bolt. The curved surface may have any shape, e.g. an oval shape, if it facilitates only handling of the machining tool. It is preferred, however, if the curved shape forms a ball. Thus, the ball does not have an adjustment function, as was the case with the prior art, but serves, as already mentioned, a facilitated placement or handling of the tool.

BRIEF DESCRIPTION OF THE DRAWING

With the above and other objects and advantages in view, the present invention will become more clearly understood in connection with the detailed description of a preferred embodiment, when considered with the accompanying drawing of which:

FIG. 1 is a blank according to the invention for producing a link according to the invention;

FIG. 1A is a front view of a pin indicating and marking the position and orientation of a screw bolt on the blank;

FIG. 2 illustrates putting a hollow cutter tool onto a head portion of the blank after having made a jaw mold for determining the position of the axis of the implant and of the bolt of the blank to be screwed in, and after having removed the marking for indicating the orientation of the axis of the bolt;

FIG. 2A a view from below onto the machining surface of the hollow cutter tool; and FIG. 3 shows the link provided with another bolt, having a threaded sleeve screwed on for holding an artificial tooth, and in a position when screwed into the implant.

DETAILED DESCRIPTION OF THE PREFERRED EMBODIMENT

In order to produce a link between a dental implant 4 (see FIG. 3) in a jaw and an artificial tooth, such as a tooth bridge, one starts with a blank R according to FIGS. 1 and 1A. This blank R comprises a first screw bolt 2 for fastening onto the dental implant 4, and a head portion 1. For reasons which will become apparent later, this head portion 1 is suitably rounded and is, in particular, spherical, as may be seen from FIG. 1.

When an implant has been inserted into a jaw of a patient, a blank R according to FIG. 1 is screwed on by means of the screw bolt 2 and is tightened. After this, a jaw mold is made by a rubber-like mass in a known manner.

Especially in the preferred embodiment where the head portion 1 is spherical, the position and orientation of the screw bolt 2 and its axis A could subsequently not be recognized by means of the mold, because only the head portion 1 protrudes from the implant. If the head portion were, however, elongated and had a longitudinal axis in continuation of the axis A, this would indicate the orientation and angular position. On the other hand, this would make later machining more difficult.

Therefore, it is preferred if an arrangement for marking the orientation of the axis A within the jaw and the implant is provided. This marking arrangement might be formed as a notch 5 (indicated in dash-dotted lines) in the spherical surface of the head portion 1, although this is not preferred. It is more favorable to indicate the orientation of the axis A by a projection 3 extending in alignment with the axis A. Such a pin-like or semi-cylindrical projection 3 gives an unequivocal trace or indentation within the rubber mold and, therefore, provides a clear indication of the position of the blank and the orientation of the axis A. The pin-like projection has to be formed in such a manner that it can be inserted in a single orientation into the recesses caused by itself in the mold.

After removing the mold, the respective blanks R are screwed off again, numbered 1 to x and are sent to a dental laboratory.

There, they can each be screwed and tightened by means of the screw bolt 2 in manipulation implants. Then, their semi-cylindrical projections are inserted into the corresponding recesses of the rubber mold so that all threads of the screw bolt 2 have the same orientation relative to the mold as they had during taking the mold from the jaw of the patient when they were completely screwed in. Then, the space up to just beneath the blank and its head 1 is filled up with a hardening mass, such as gypsum, in order to fix the position of the blank and the orientation of the axis A of the screw bolt 2 which was previously determined by means of the pin 3, and which corresponds to the position of the implant within the jaw of the respective patient.

The situation is represented in FIG. 2 where a dash-dotted line G indicates the level of the gypsum bed. For the sake of simplicity, the manipulation implant of the laboratory is omitted in FIG. 2. Moreover, the marking pin 3 was sawed off, which is no longer necessary after removal of the mold, so that a smooth ball presents its surface. It may be seen that smoothness would be affected if the notch 5 were used to mark the orientation of the axis A.

If, in this situation, a machining tool, such as the hollow cutter tool 6 shown in FIGS. 2 and 2A, is lowered along a precisely vertical axis S onto the ball 1, it will cut a further bolt 7 out of the ball 1 which can then be provided with a thread, as may be seen from FIG. 3. The bolt 7 will then extend precisely along the axis S, and this will intersect with the axis A in the center point of the ball, the two axes A, S forming an angle with each other which is determined by the position of the implant 4 within the jaw of the patient, on the one hand, and by the desired orthogonal position of the respective artificial tooth, on the other hand.

To this end, the hollow cutter 6 has both frontal machining edges 8 and inner machining edges 9 forming a hollow cylinder. The result of such machining may be seen from FIG. 3 where the finished link B is represented as being already inserted into the implant 4 of the patient. After tightening the screw bolt 2 in the implant of the jaw, the two screw bolts 2 and 7 are in a fixed, and therefore immovable, but also correct angular orientation ensured by the previously discussed steps. From the foregoing machining, this link B still has a portion 1' in the form of a ball segment, a ball surface 1" facing the first screw bolt, while the other screw bolt 7 has a length which corresponds to more than half, e.g. ⅔ of the whole spherical surface (cf. FIGS. 1, 2) which forms also the ball surface 1". It may be convenient that the two bolts 2, 7 have opposite threads, e.g. to provide a left-handed thread on the bolt 7.

Onto this screw bolt 7, a nut or tooth sleeve 10 may be screwed on that is attached to the respective artificial tooth, such as the above-mentioned bridge, and which has an edged cross-section, e.g. a squared one or, preferably, a hexagonal one, for better handling it at the end having the opening. The bridge is then, for example, cemented onto this nut sleeve. By aligning all axes S of blanks of a mold parallel to each other after machining to form links, an artificial tooth having corresponding bores may be placed over them without any problem.

In addition, by having an end portion of the nut sleeve 10 which faces the jaw and comprises an edged cross-section, this enables also easier detachment in case it is necessary. It would then be engaged by a screw spanner and turned with respect to the thread of the bolt 7. The high torque which can be attained enables release of the connection or cemented connection between the tooth sleeve or nut sleeve and the artificial tooth. After releasing all sleeves, the bridge merely has to be lifted. On the other hand, the method according to the invention enables a joint to be established under various angles of inclination with respect to a vertical plane in a simple and tough manner where attaching and detaching present no problem.

By carefully carrying out the method described, it is ensured that the threads of the manipulation implants are arranged within the gypsum mold in an identical manner with those threads of the implants fastened to the jaw. Therefore, the further bolt or screw bolt 7 of the blank in the gypsum mold will be oriented in the desired direction after having completely screwed the link B into an implant in the jaw. If, for example, a damaged link has to be replaced later, a new one can be produced from a new blank directly in a gypsum mold. After releasing the tooth sleeves and lifting the artificial tooth, the damaged link is screwed out of the implant and is replaced by a new one. Then, the tooth sleeve and the artificial tooth may be placed on it immediately again.

I claim:

1. A link to be inserted between a dental implant in a jaw and an artificial tooth, comprising
    a first screw bolt for fastening said link on said dental implant,
    a head portion in form of a second screw bolt for fastening a tooth holding sleeve, said screw bolts formed as a unitary one-piece construction, where the mutual angular orientation of both screw bolts is adapted to the jaw, on the one hand, and to the orientation of said artificial tooth, on the other hand.

2. Link as claimed in claim 1, further comprising an intermediate portion between said first and second screw bolts, said intermediate portion having a ball segment-like shape to form a spherical surface which faces said first screw bolt.

3. Link as claimed in claim 2, wherein said second screw bolt has a length which corresponds to a length extending over more than one-half of a diameter of the ball.

4. Link as claimed in claim 3 wherein the length of said second screw bolt corresponds to about ⅔ of the diameter of the ball.

5. A blank for forming a link comprising
    a first screw bolt for fastening it on a dental implant, said first screw bolt having a longitudinal axis;
    a head portion formed as an integral part with said first screw bolt, said head portion serving for a cutting out of a second screw bolt having an orientation which is selectable relative to said axis of said first screw bolt; and
    a marking arrangement on said head portion for unequivocally marking the orientation of said first screw bolt.

6. Blank as claimed in claim 5 wherein said marking arrangement is formed by an elongated projection extending as a prolongation of the axis of said first screw bolt.

7. Blank as claimed in claim 6, wherein said marking arrangement is formed by a pin-like structure having an asymmetrical cross-section to produce an impression when inserted into a mold material.

8. Blank as claimed in claim 7, wherein said asymmetrical cross-section is a semi-cylindrical cross-section.

9. A method for producing a link to be inserted between a dental implant in a jaw and an artificial tooth, comprising the steps of
    providing a blank having a screw bolt and a head portion connected to said bolt;
    providing a machining tool having a longitudinal axis;
    putting said blank in such an angular orientation relative to the axis of said tool, that said screw bolt assumes a position corresponding to the orientation of the jaw and of the implant fastened therein; and
    forming at least part of said head portion to the shape of another bolt by said machining tool and providing it with an outer thread.

10. Method as claimed in claim 9, wherein a hollow cutter is used as said machining tool, the hollow interior of it leaving the bolt to be finished when machining said head portion.

11. Method as claimed in claim 9, wherein said head portion has a curved surface.

12. Method as claimed in claim 11, wherein said head portion has an at least partially spherical surface.

13. Method as claimed in claim 9, wherein said blank together with said bolt and the joining head portion is first put into a hardening mass as a holding basis for said position, and said forming step is carried out after hardening.

14. Method as claimed in claim 13, wherein said hardening mass is gypsum.

15. Method as claimed in claim 9 wherein said forming step is carried out over a length corresponding to a length longer than up to the center of the head portion.

16. Method as claimed in claim 9, further comprising the steps of inserting said blank into said dental implant for determining the orientation of the jaw and of the implant fastened therein;

marking said orientation by a marking arrangement;

taking a mold of said jaw together with said blank and said marking arrangement to obtain an impression also of the latter;

removing said mold and said blank from the jaw;

fixing said blank in a manipulation implant using the mold and said impression as an orientation aid; and carrying out said forming step.

17. Method as claimed in claim 16, wherein said step of fixing comprises casting a hardening mass.

18. Method as claimed in claim 16, further comprising the step of removing said marking arrangement from said blank before said forming step.

19. Method as claimed in claim 18, wherein said forming step is carried out over ⅔ the length of said head portion.

20. A blank for forming a link between a dental implant and a tooth, comprising a first screw bolt to be fastened on the dental implant, said first screw bolt having a longitudinal axis;

a head portion formed as a unitary one-piece construction with said screw bolt, said head portion serving for the formation of a second bolt angled to said axis;

wherein said head portion includes a marking structure for marking an orientation of said axis, said marking structure being formed as a unitary one-piece construction with said head portion.

\* \* \* \* \*